(12) United States Patent  
Rauchwerger et al.

(10) Patent No.: US 10,383,655 B2  
(45) Date of Patent: Aug. 20, 2019

(54) WIRE-GUIDED SURGICAL INSTRUMENT

(71) Applicant: Ambitus Medical Supplies LLC, Oceanside, NY (US)

(72) Inventors: Jacob Jeffrey Rauchwerger, Cedarhurst, NY (US); Ari Isaacs, Oceanside, NY (US)

(73) Assignee: AMBITUS MEDICAL SUPPLIES LLC, Oceanside, NY (US)

( * ) Notice: Subject to any disclaimer, the term of this patent is extended or adjusted under 35 U.S.C. 154(b) by 341 days.

(21) Appl. No.: 14/897,294

(22) PCT Filed: Aug. 6, 2014

(86) PCT No.: PCT/US2014/049913  
§ 371 (c)(1),  
(2) Date: Dec. 10, 2015

(87) PCT Pub. No.: WO2015/021132  
PCT Pub. Date: Feb. 12, 2015

(65) Prior Publication Data  
US 2016/0128713 A1 May 12, 2016

Related U.S. Application Data

(60) Provisional application No. 61/952,386, filed on Mar. 13, 2014, provisional application No. 61/864,070, filed on Aug. 9, 2013.

(51) Int. Cl.  
*A61B 17/3211* (2006.01)  
*A61B 17/3213* (2006.01)  
(Continued)

(52) U.S. Cl.  
CPC ...... *A61B 17/3211* (2013.01); *A61B 17/3213* (2013.01); *A61B 17/3215* (2013.01);  
(Continued)

(58) Field of Classification Search  
CPC ............... A61B 17/0482; A61B 17/32; A61B 17/320052; A61B 17/3205;  
(Continued)

(56) References Cited

U.S. PATENT DOCUMENTS 3,754,693 A 8/1973 Herr  
4,633,860 A 1/1987 Korth et al.  
(Continued)

FOREIGN PATENT DOCUMENTS

CN 202776486 U 3/2013  
EP 2 138 200 12/2009  
(Continued)

OTHER PUBLICATIONS

International Search Report and Written Opinion dated Jun. 13, 2013, from PCT/US2013/027272.  
(Continued)

*Primary Examiner* — Todd J Scherbel  
(74) *Attorney, Agent, or Firm* — Katten Muchin Rosenman LLP

(57) ABSTRACT

Disclosed herein is a surgical instrument having a cylindrical tube affixed thereto. A guidewire can be threaded through the cylindrical tube to allow for advancement of the surgical instrument to a surgical site.

8 Claims, 7 Drawing Sheets

(51) Int. Cl.
    *A61B 17/3209*     (2006.01)
    *A61B 17/3215*     (2006.01)
    *A61B 17/22*     (2006.01)
    *A61B 17/00*     (2006.01)

(52) U.S. Cl.
    CPC ............ *A61B 17/32093* (2013.01); *A61B 2017/00477* (2013.01); *A61B 2017/22039* (2013.01); *A61B 2017/32113* (2013.01)

(58) Field of Classification Search
    CPC .......... A61B 17/3209; A61B 17/32093; A61B 17/3211; A61B 17/3403; A61B 2017/32113; A61B 2017/22038; A61B 2017/22039; A61B 2017/22041; A61B 2017/3405
    See application file for complete search history.

(56) References Cited

U.S. PATENT DOCUMENTS

| | | | |
|---|---|---|---|
| 4,955,890 | A | 9/1990 | Yamamoto et al. |
| 5,250,063 | A | 10/1993 | Abidin et al. |
| 5,599,351 | A | 2/1997 | Haber et al. |
| 5,843,108 | A | 12/1998 | Samuels |
| 7,341,596 | B2 | 3/2008 | Heppler |
| 8,016,845 | B1 | 9/2011 | Sauer |
| 8,925,443 | B2 | 1/2015 | Agarwal et al. |
| 9,743,950 | B2 * | 8/2017 | Rauchwerger ..... A61B 17/3211 |
| 2003/0144674 | A1 * | 7/2003 | Loubens ............. A61B 17/062 606/148 |
| 2004/0181246 | A1 | 9/2004 | Heppler |
| 2005/0177183 | A1 | 8/2005 | Thorne et al. |
| 2005/0240165 | A1 | 10/2005 | Miki et al. |
| 2008/0077146 | A1 | 3/2008 | Pernsteiner et al. |
| 2012/0226299 | A1 | 9/2012 | Heppler |

FOREIGN PATENT DOCUMENTS

| | | |
|---|---|---|
| EP | 2 311 394 A1 | 4/2011 |
| JP | 2008-67810 | 3/2008 |
| WO | 93/25152 | 12/1993 |
| WO | 93/25152 A1 | 12/1993 |
| WO | 2012/044633 A1 | 4/2012 |
| WO | 2013/126661 A1 | 8/2013 |
| WO | 2013126661 A1 | 8/2013 |

OTHER PUBLICATIONS

International Search Report and Written Opinion dated Nov. 20, 2014, from PCT/US2014/049913.
Office Action dated Oct. 20, 2015, from U.S. Appl. No. 13/774,009.
Office Action dated Jul. 2, 2015, from U.S. Appl. No. 13/774,009.
Office Action dated Apr. 29, 2015, from U.S. Appl. No. 13/774,009.
Communication Pursuant to Article 94(3) EPC dated Jul. 5, 2017, from the corresponding EP 14 835 391.5-1659.
Supplementary European Search Report dated Nov. 28, 2016, from the corresponding EP Application No. 14835391.5.
U.S. Office Action dated Sep. 21, 2016, from the corresponding U.S. Appl. No. 13/774,009.
First Office Action dated Nov. 24, 2017, from the corresponding Chinese Application No. 201480055847.8.
U.S. Office Action dated Jul. 2, 2015, from the corresponding U.S. Appl. No. 13/774,009.
U.S. Office Action dated Oct. 20, 2015, from the corresponding U.S. Appl. No. 13/774,009.
U.S. Office Action dated Apr. 20, 2016, from the corresponding U.S. Appl. No. 13/774,009.
Notice of Allowance dated Apr. 19, 2017, from the corresponding U.S. Appl. No. 13/774,009.
Second Office Action dated Jul. 17, 2018, from the corresponding Chinese Application No. 201480055847.8, 18 sheets.
Third Office Action dated Jan. 11, 2019, from the corresponding Chinese Application No. 201480055847.8, 4 sheets.

* cited by examiner

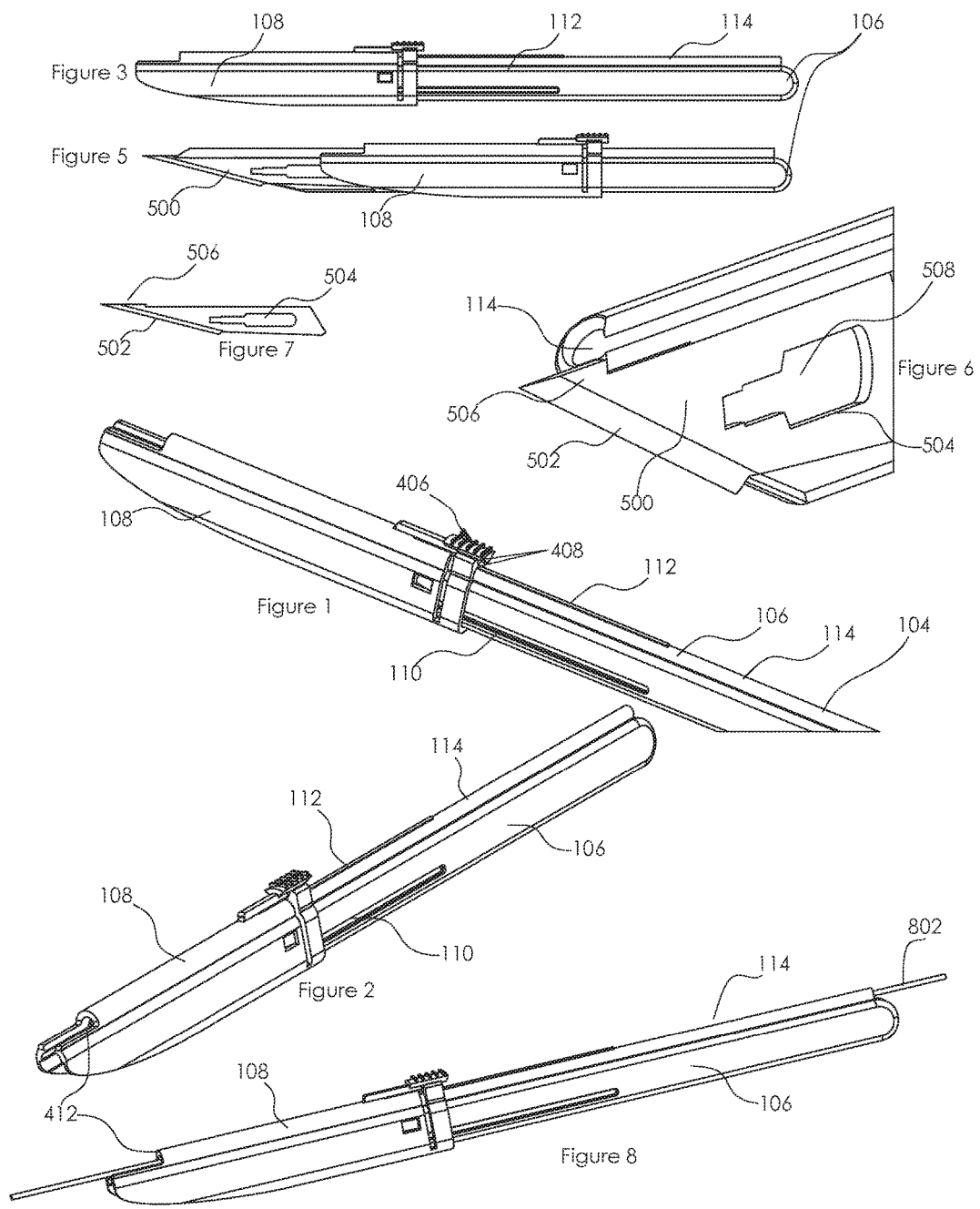

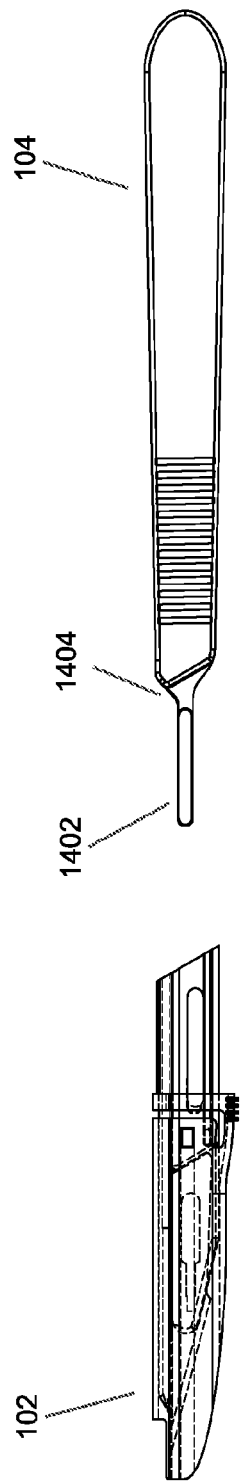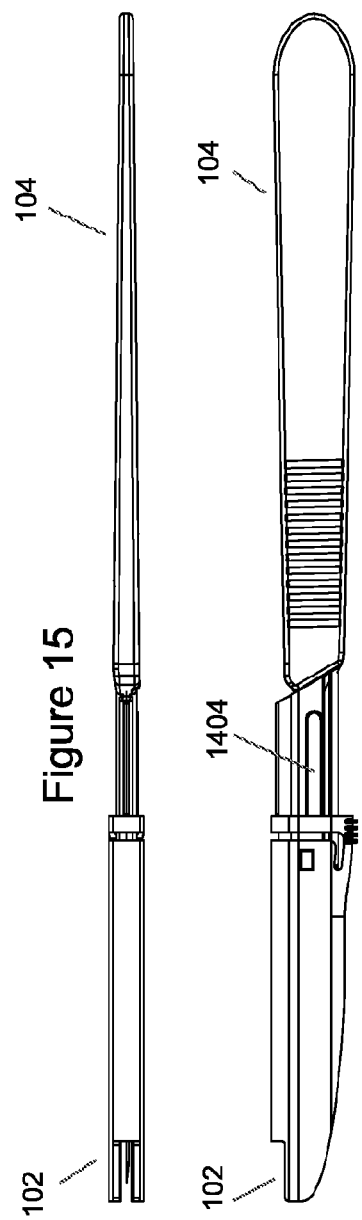

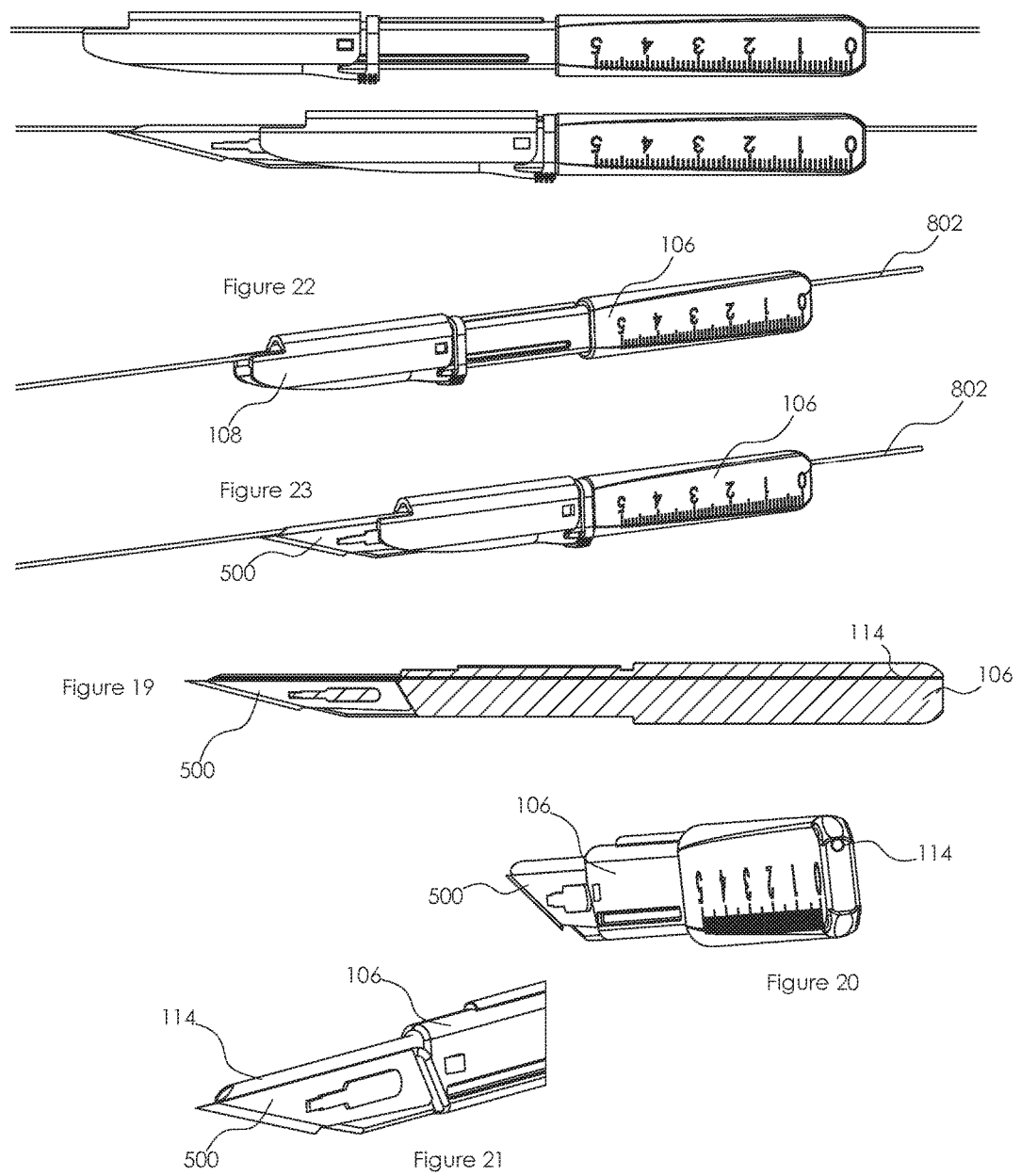

WIRE-GUIDED SURGICAL INSTRUMENT

CROSS REFERENCE TO RELATED APPLICATIONS

The present application claims priority to U.S. Provisional Application Nos. 61/864,070, filed Aug. 9, 2013 and 61/952,386, filed Mar. 13, 2014, the entire contents of which are incorporated by reference in their entirety.

FIELD OF THE INVENTION

The invention is directed to a surgical instrument having a cylindrical tube for accommodating a guidewire therein.

BACKGROUND OF THE INVENTION

Surgical instruments, such as scalpels, are used to make an incision in the skin, enabling insertion of devices whose purpose is to deliver various substances to the body. In order to minimize the size of the incision, a guidewire is inserted into the body cavity and instruments can be reliably advanced over the guidewire and into the body cavity for proper placement. This method is known as the "Seldinger Technique." In many circumstances, the guidewire incision needs to be widened in order to accommodate larger medical devices such as a trocar or catheter. The enlargement is typically done by hand which may lead to an imprecise or larger than needed cut. Therefore, a need clearly exists for a surgical instrument capable of using the guidewire to aid a surgical device, such as a scalpel, in making a more precise incision

BRIEF DESCRIPTION OF THE DRAWINGS

FIGS. 1 and 2 are perspective views of the surgical instrument.

FIG. 3 is a side view of the surgical instrument of FIGS. 1 and 2.

FIG. 5 is a side view of the surgical instrument after the blade of the surgical instrument has been exposed.

FIG. 6 is a cutaway view of the blade of the surgical instrument.

FIG. 7 is a side view of the blade of the surgical instrument.

FIG. 8 shows the device with the guide wire inserted as it will be during the procedure.

FIGS. 13-15 are views of another alternate embodiment of the surgical instrument in which the handle is detachable.

FIGS. 19-23 are views of another alternate embodiment of the invention wherein the cylindrical tube is an over molded metal tube.

DETAILED DESCRIPTION OF THE INVENTION

Figure 4:
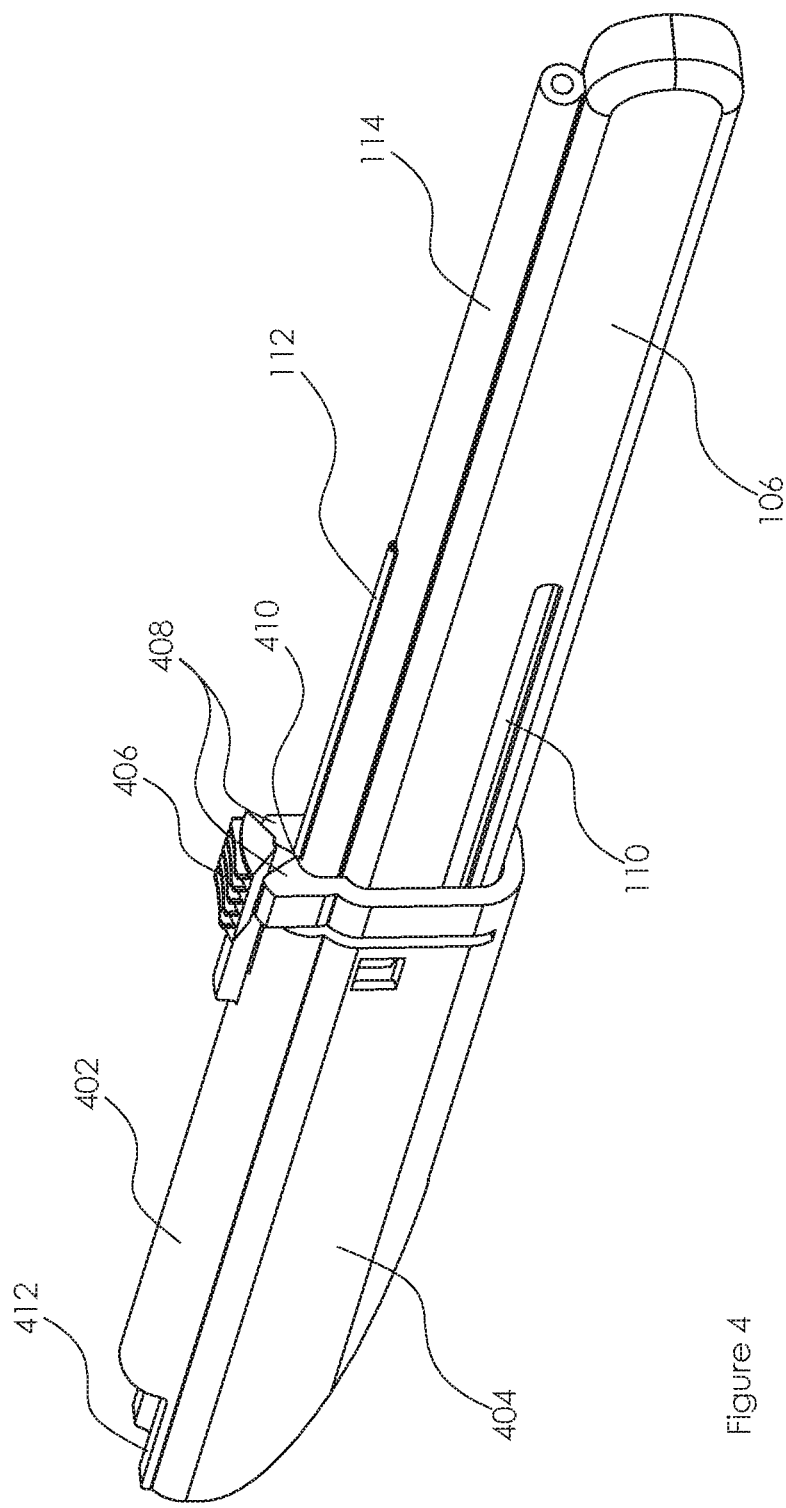
FIG. 4 is an enlarged rear ¾ view to illustrate one possible locking mechanism for the sliding cover

With reference to FIGS. 1-3, depicted is surgical instrument 100 having proximal end 102 and distal end 104. Surgical instrument 100 generally comprises body 106 and cover 108. The distal end 104 of surgical instrument 100 is formed as a handle to allow a user to grip and operate the surgical instrument. In a preferred embodiment, body 106 and cover 108 are formed from a surgical grade plastic material. However, any suitable material, such as stainless steel or other plastic/metal, may also be used.

Body 106 comprises grooves 110 and raised stop 112. Detents formed on cover 108 (not shown) interlock with grooves 110 to allow cover 108 to slide over body 106 from a closed position (FIG. 3) to an open position (FIG. 4). Raised stop 112 prevents cover 108 from being moved to an open position without intervention by a user.

Body 106 further comprises a cylindrical tube 114 attached to a top surface of body 106. Preferably, cylindrical tube 114 is formed integral to body 106 and extends substantially the entire length of body 106. This allows a guidewire to extend behind the operator of surgical instrument 100 so it minimizes interference with a user. The proximal end of cylindrical tube 114 is preferably beveled (FIG. 5). The advantage of the bevel is that it results in a sharp tipped channel for cylindrical tube 114, allowing the channel to pass through the skin and soft tissue as the clinician makes a dermototomy incision.

The diameter of cylindrical tube 114 is great enough such that a guidewire may easily be passed therethrough. Only the first several millimeters of the cylindrical tube 114 channel need to be precisely fit the guidewire diameter to ensure that blade 500 is located close to the guidewire. The remaining portion of cylindrical tube 114 may have a wider diameter to minimize friction with the guidewire during advancement of surgical instrument 100.

Cover 108 is sized such that it surrounds body 106 as shown in FIG. 1-3. Cover 108 comprises channel 402 which is formed so to easily accommodate and slide over raised stop 112 and cylindrical tube 114. Sidewalls 404 extend downward from channel 402. Each sidewall 404 has a detent (not shown) that interlocks with grooves 110. In order to move cover 108 from a closed position (FIG. 3) to an open position (FIG. 5), a user presses button 406 (see FIG. 4). This causes tangs 408 to open outward, away from body 106. This forms a channel 410 which allows cover 108 to advance without being hindered by raised stop 112.

Once tangs 408 advance past the end of raised stop 112, tangs 108 return to their initial closed configuration. Now, the surgical device 100 is in an open position as shown in FIG. 5 and cover 108 is locked in this new open position. The length of channels 110 determines how securely that cover 108 is locked in both the open and closed positions of surgical device 100. Preferably, grooves 110 and raised stop 112 are the same length and begin/end at the same location on body 106.

When surgical device 100 is in an open position, blade 500 is exposed. Blade 500 is depicted in FIGS. 5-7. As shown, blade 500 comprises cutting edge 502, opening 504, and raised edge 506. Opening 504 is sized such that it locks onto a corresponding button 508 on body 106. This allows blade 500 to be securely attached to body 106. Raised edge 506 allows the tip of cutting edge 502 to extend close to the end of cylindrical tube 112, thus facilitating the centering of the guidewire with blade 500. Further, raised edge 506 allows a guidewire passed through cylindrical tube 114 to rest flush against the non-cutting edge of blade 500, eliminating any gaps between the guidewire wire and blade 500.

Blade 500 may be made from any suitable material that is able to retain a sharp, surgical edge such as stainless steel, ceramic, etc.

Referring again to FIGS. 4, cover 108 additionally comprises cutout portion 412 which provides a user access to cylindrical tube 114 to thread the guidewire even when the surgical instrument 100 is in a closed position to minimize the risk of operator injury. The portion of cover 108 which extends in the proximal direction past cylindrical tube 114 serves to protect a user from blade 500 while still allowing easy access to cylindrical tube 114.

To use surgical instrument 100, a guidewire 802 is first threaded through cylindrical tube 114 as shown in FIG. 8. Next, the surgical instrument is opened as described with reference to FIGS. 3-5 to expose blade 500. The surgical instrument 100 can then be advanced over guidewire 802 to a skin surface in order to make an incision. Because surgical instrument 100 is relatively thin and has no side protrusions extending from it, surgical instrument 100 can easily be advanced through an incision without causing much trauma to adjacent tissue.

Figure 12:
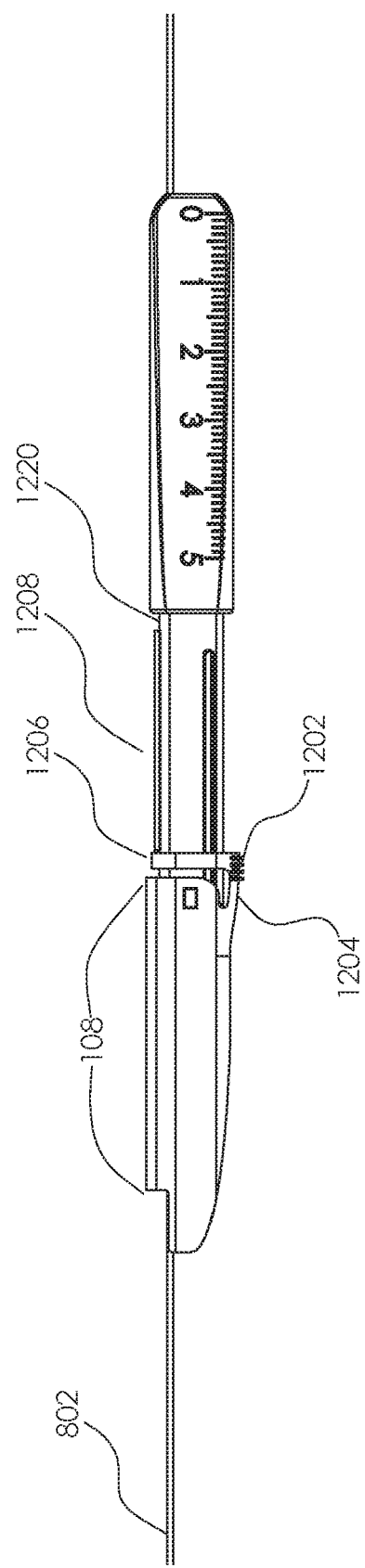
FIG. 12 is a view of an alternate embodiment of the surgical instrument.

FIG. 12 depicts an alternate embodiment of surgical device 100 having a different mechanism for opening and closing cover 108. In this embodiment, cover 108 comprises button 1202, flexible member 1204, ledge 1206, and hump 1208. Preferably, ledge 1206 is u-shaped and extends around both sides of surgical device 100 and is connected to button 1202. Hump 1208 is preferably a semi-circular ridge extending along a top edge of surgical device 100. Flexible member 1204 is preferably constructed from a flexible, resilient material (e.g., a plastic) which can survive multiple bends.

Pressing button 1202 causes flexible member 1204 to flex toward cover 108, which in turn raises ledge 1206 over hump 1208. Cover 108 can then be slid to position 1210 (at an end of hump 1208). Here, flexible member 1204 returns to its initial unflexed position, thereby preventing further movement of cover 108.

FIGS. 13-15 depict another alternate embodiment of surgical device 100 in which the proximal end 104 can be separated from distal end 104. In this embodiment, distal end 104 comprises detent member 1402 which extends from protrusion 1404. Preferable, detent member 1402 has a width greater than that of protrusion 1404 and is made of stainless steel or hard plastic. Distal end 102 comprises cutout portion 1406 which is sized to accommodate detent member 1402. When proximal end 104 is attached to distal end 104, detent member 1402 locks into cutout portion 1406, thus firmly locking both ends together. By using this configuration, distal end 104 can be used repeatedly while proximal end 102 can be disposed after use. It should be obvious that the shape of detent member 1402 can be modified to fit onto any variety of existing detachable scalpel handles.

Device Manufacture

Figure 10:
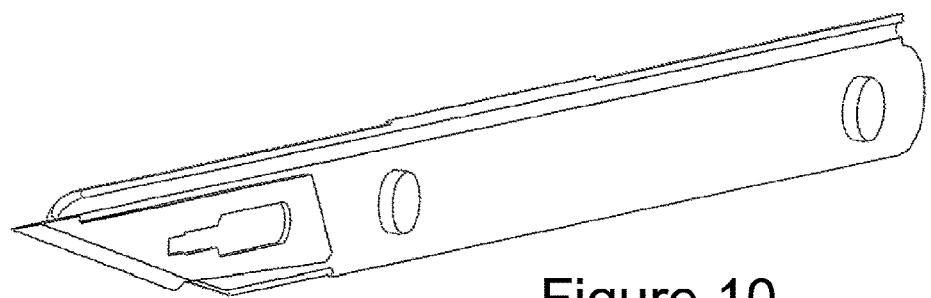
FIGS. 10 and 11 are perspective views of a second half of the surgical instrument in an unassembled state.
Figure 11:
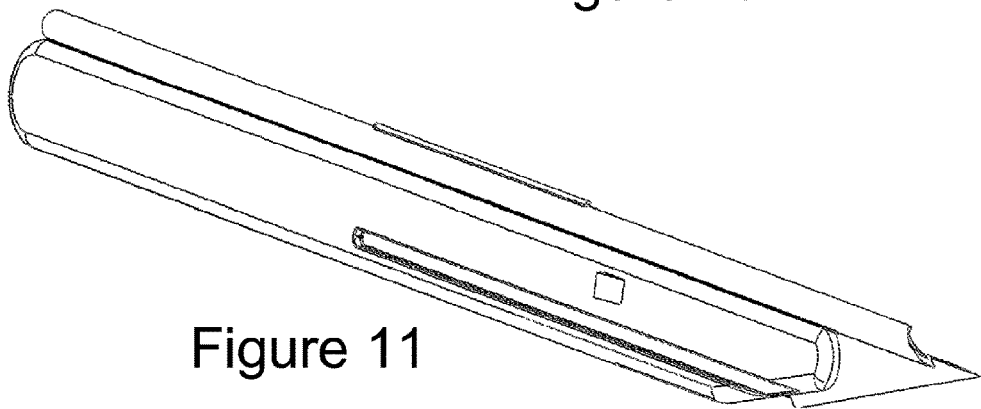
Figure 9:
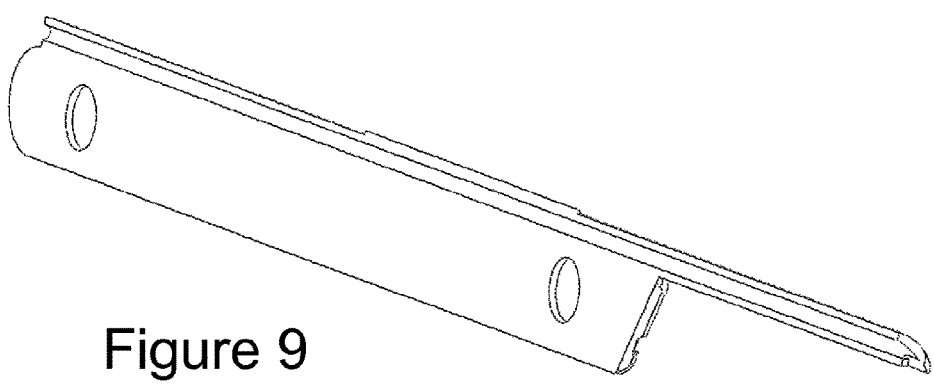
FIG. 9 is a perspective view of a first half of the surgical instrument in an unassembled state.

Due to the manufacturing difficulties in molding a long narrow slot like cylindrical tube 114, it is preferable to manufacture body 106 in two halves which can later be joined using sonic welding, adhesive, or any other known methods to secure the two halves. Examples of the two halves that may be joined to form body 106 are depicted in FIGS. 9-11.

Figure 16:
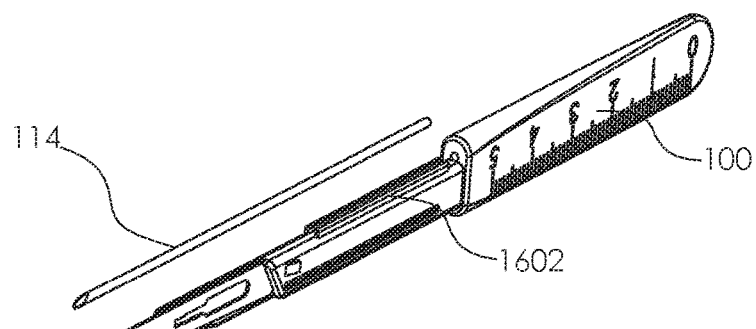
FIGS. 16-18 are views of an alternate embodiment of the invention where the cylindrical tube is detachable/replaceable.
Figure 17:
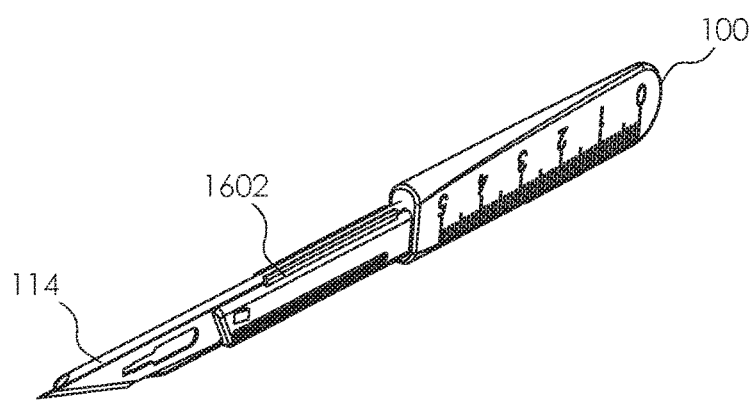
Figure 18:
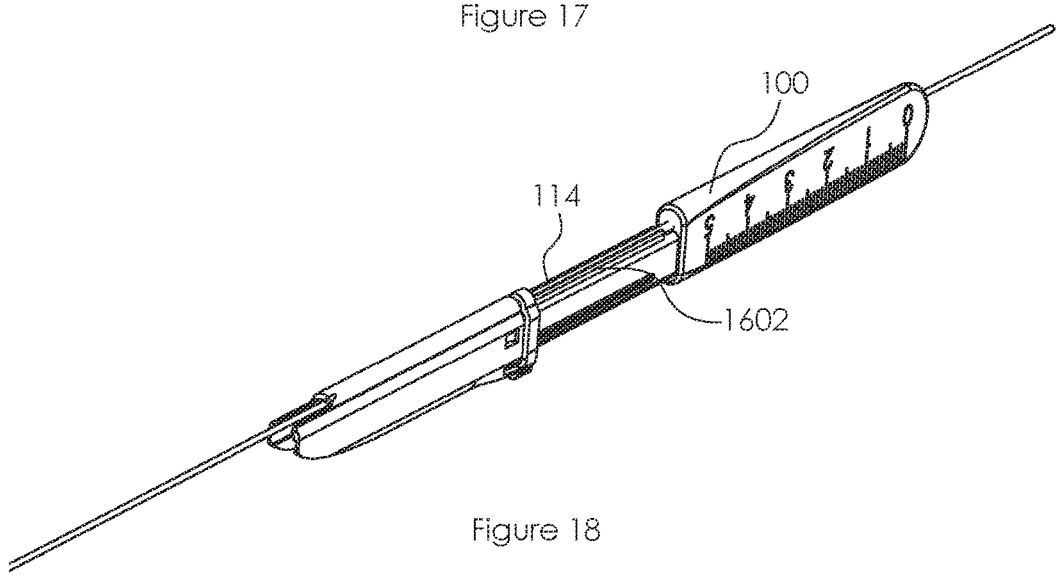

Another possible method of overcoming these manufacturing difficulties is to manufacture the handle without the channel but with provisions to accommodate a separately manufactured tube to be added. For example, as depicted in FIGS. 16-18, surgical device 100 can be manufacture without cylindrical tube 114 (FIG. 16). Cylindrical tube 114 can be manufactured in a separate process and added to surgical device 100 by inserting cylindrical tube 114 into retaining channel 1602 (FIGS. 17 and 18). Other connection techniques, such as a snap fit connection, can also be utilized.

In some embodiments, it may be desirable to permanently connect cylindrical tube 114 to surgical device 100. For example, as shown in FIG. 19, cylindrical tube 114 may run the entire length of surgical device 100. To accomplish this configuration, cylindrical tube 114, which is preferably stainless steel in this embodiment, is placed in a mold for body 106. Cylindrical tube 114 is then over molded so that it is encased in body 106 (i.e., cylindrical tube 114 is inserted into the mold and then plastic is injected around it). As shown in FIG. 20, the cylindrical tube 114 extends to the back of body 106. Further, as shown in FIG. 21, the front of cylindrical tube 114 protrudes over blade 500. A guidewire 802 can be inserted through cylindrical tube 114 as shown in FIGS. 22 and 23 and surgical device 100 can be used as previously described.

This embodiment of surgical device 100 is similar to that depicted in FIGS. 1-8. However, in this embodiment, cylindrical tube 114 is a metal tube that has been integrated into body 106 instead of a molded channel. However, the change in manufacturing does not affect the use of surgical device 100.

What is claimed is:

1. A surgical instrument for advancement over a preinserted guidewire as used during performance of the Seldinger or modified Seldinger techniques, the surgical instrument comprising:
   a closed cylindrical tube;
   a rigid body having a proximal end and a distal end;
   wherein a portion of the closed cylindrical tube is immovably encased within a top portion of the distal end of the rigid body,
   wherein a first end of the closed cylindrical tube located near a tip of the blade has a beveled tip; and
   a blade located at the proximal end of the rigid body,
   wherein an exterior, non-cutting edge of the blade extends along a surface of the closed cylindrical tube,
   wherein the closed cylindrical tube is configured to be threaded over the preinserted guidewire by inserting the preinserted guidewire into a proximal end of the closed cylindrical tube near the tip of the blade and the surgical instrument is advanced over the preinserted guidewire to a skin surface to perform a dermototomy incision during the Seldinger or modified Seldinger techniques using a cutting edge of the blade.

2. The surgical instrument of claim 1, wherein a portion of the cylindrical tube not encased within the top portion of the distal end of the rigid body is affixed to a channel located on the proximal end of the rigid body.

3. The surgical instrument of claim 1, further comprising:
   a blade attachment protrusion located on the proximal end of the rigid body; and
   a hole located within the blade,
   wherein the hole located within the blade is sized for a snap fit connection to the blade attachment protrusion to allow the blade to be removably attached to the rigid body.

4. The surgical instrument of claim 1, wherein the closed cylindrical tube is made from stainless steel.

5. The surgical instrument of claim 1, further comprising:
   a cover movable between an open position and a closed position,
   wherein the cover covers the blade in the closed position and exposes the blade in the open position, and
   wherein the cover slides from the open position to the closed position in a groove located on the rigid body.

6. The surgical instrument of claim 5, wherein the cover comprises a raised channel for sliding over the closed cylindrical tube.

7. The surgical instrument of claim 1, wherein the closed cylindrical tube is encased by overmolding.

8. A surgical instrument for advancement over a preinserted guidewire as used during performance of the Seldinger or modified Seldinger techniques, the surgical instrument consisting essentially of:
- a closed cylindrical tube;
- a rigid body having a proximal end and a distal end;
- wherein a portion of the closed cylindrical tube is encased within a top portion of the distal end of the rigid body; and
- a blade located at the proximal end of the rigid body,
- wherein a first end of the closed cylindrical tube does not extend beyond a tip of the blade and a second end of the closed cylindrical tube coincides with an end of the distal end of the rigid body,
- wherein an exterior, non-cutting edge of the blade extends along a surface of the closed cylindrical tube.

* * * * *